(12) United States Patent
Honda et al.

(10) Patent No.: US 8,436,198 B2
(45) Date of Patent: May 7, 2013

(54) FLUORINE-CONTAINING N-ALKYLSULFONYLIMIDE COMPOUND, MANUFACTURING METHOD THEREFOR, AND METHOD OF MANUFACTURING AN IONIC COMPOUND

(75) Inventors: Tsunetoshi Honda, Akita (JP); Hiroyuki Yatsuyanagi, Yurihonjo (JP); Takashi Konishi, Akita (JP); Daisuke Takano, Akita (JP)

(73) Assignees: Mitsubishi Materials Corporation, Tokyo (JP); Mitsubishi Materials Electronic Chemicals Co., Ltd., Akita-Shi (JP)

( * ) Notice: Subject to any disclaimer, the term of this patent is extended or adjusted under 35 U.S.C. 154(b) by 0 days.

(21) Appl. No.: 13/138,742

(22) PCT Filed: Mar. 31, 2010

(86) PCT No.: PCT/JP2010/002345
§ 371 (c)(1),
(2), (4) Date: Sep. 23, 2011

(87) PCT Pub. No.: WO2010/113492
PCT Pub. Date: Oct. 7, 2010

(65) Prior Publication Data
US 2012/0022269 A1 Jan. 26, 2012

(30) Foreign Application Priority Data
Mar. 31, 2009 (JP) .................. 2009-084284

(51) Int. Cl.
*C07C 309/05* (2006.01)
(52) U.S. Cl.
USPC ........................................................... 558/61
(58) Field of Classification Search ............... 558/61
See application file for complete search history.

(56) References Cited

FOREIGN PATENT DOCUMENTS
WO WO-2007/091817 A1 8/2007

OTHER PUBLICATIONS

Johann N. Meubdoerffer et al., "Bis-perfluoroalkanesulfonimides (RfSO2)2NH," Chemiker- Zeitung, 96, Jahrgang (1972) Nr. 10, pp. 582-583 and English translation thereof.*
John K. Ruff, "The Imidodisulfuryl Fluoride Ion," Inorganic Chemistry, 1965, pp. 1446-1449.*
Jie Zhang et al., "Direct methylation and trifluoroethylation of imidazole and pyridine derivatives," Chem. Comm., 2003, pp. 2334-2335.*
C. B. Colburn et al., "Reactions of Imidobis (Sulfuryl Fluoride) and N-Chloroimidobis (Sulfuryl Fluoride) with Olefins," Journal of Fluorine Chemistry, 1981, No. 17, pp. 75-84.*
Jie Zhang et al., "Direct methylation and trifluoroethylation of imidazole and pyridine derivatives," Chem Comm., 2003, pp. 2334-2335.
Johann N. MeuBdoerffer et al., "Bis-perfluoroalkanesulfonimides (R4SO2)2NH," Chemiker-Zeitung, 96, Jahrgang (1972) Nr. 10, pp. 582-583 and English translation thereof.
C. B. Colburn et al., "Reactions of Imidobis (Sulfuryl Fluoride) and N-Chioroimidobis (Sulfuryl Fluoride) with Olefins," Journal of Fluorine Chemistry, 1981, 17, pp. 75-84.
International Search Report dated May 18, 2010, issued for PCT/JP2010/002345 and English translation thereof.

* cited by examiner

*Primary Examiner* — Kamal Saeed
*Assistant Examiner* — Janet L Coppins
(74) *Attorney, Agent, or Firm* — Edwards Wildman Palmer LLP; James E. Armstrong, IV; Nicholas J. DiCeglie, Jr.

(57) ABSTRACT

According to the method for producing fluorine-containing N-alkylsulfonylimide compound, the fluorine-containing N-alkylsulfonylimide compound can be produced safely with a high recovery rate by alkylating fluorine-containing sulfonylimide acid or fluorine-containing sulfonylimide acid salt with dialkylsulfuric acid or dialkylcarbonic acid.

18 Claims, No Drawings

FLUORINE-CONTAINING N-ALKYLSULFONYLIMIDE COMPOUND, MANUFACTURING METHOD THEREFOR, AND METHOD OF MANUFACTURING AN IONIC COMPOUND

TECHNICAL FIELD

The present invention relates to a fluorine-containing N-alkylsulfonylimide compound, a method of producing a fluorine-containing N-alkylsulfonylimide compound, and a method of producing an ionic compound.

Priority is claimed on Japanese Patent Application No. 2009-084284, filed Mar. 31, 2009, the content of which is incorporated herein by reference.

BACKGROUND ART

As an N-alkyl bis(perfluoroalkylsulfonyl)imide that is a sulfonic acid derivative, the N-methyl bis(trifluoromethanesulfonyl)imide whose alkyl group is methyl group ($CH_3$) and perfluoroalkyl group is trifluoromethyl group ($CF_3$), and the N-methyl bis(nonafluorobutanesulfonyl)imide whose alkyl group is a methyl group ($CH_3$) and a perfluoroalkyl group is a nonafluorobutyl group ($C_4F_9$), have been known.

As methods for producing N-alkyl bis(perfluoroalkylsulfonyl)imide, the methods disclosed in Non Patent Literature (NPL) 1 and NPL 2 are known. Specifically, in the method disclosed in NPL 1 for producing N-methyl bis(perfluoroalkylsulfonyl)imide, bis(perfluoroalkylsulfonyl)imide acid is methylated using trimethyl orthoacetate ($CH_3C(OCH_3)_3$)) as a methylating agent. In the method disclosed in NPL 1, trifluoromethyl group ($CF_3$) and nonafluorobutyl group ($C_4F_9$) are used as a perfluoroalkyl group.

In the method disclosed in NPL 2 for producing N-methyl bis(perfluoroalkylsulfonyl)imide, bis(perfluoroalkylsulfonyl)imide acid is methylated using diazomethane ($CH_2N_2$) as a methylating agent. In the method disclosed in NPL 2, nonafluorobutyl group ($C_4F_9$) is used as a perfluoroalkyl group.

In addition, as an N-alkyl bis(fluorosulfonyl)imide, N-methyl bis(fluorosulfonyl)imide, which has a methyl group as an alkyl group, and N-ethyl bis(fluorosulfonyl)imide, which has an ethyl group as an alkyl group are known. As methods for producing them, the methods, in which bis(fluorosulfonyl)imide silver salt and alkyl iodide are reacted, described in NPL 3 is known.

RELATED ART DOCUMENT

Non-Patent Literature

[NPL1] CHEM. COMMUN., 2003, 2334-2335
[NPL2] Chemiker-Zeitung, 96. Jahrgang (1972) Nr. 10
[NPL3] Inorganic Chemistry, Vol. 4, No. 10, 1965, 1446-1449

DISCLOSURE OF INVENTION

Technical Problem

In the method for producing N-methyl bis(perfluoroalkylsulfonyl)imide disclosed in NPL 1, a side reaction where the trimethyl orthoacetate, which is an methylating agent, is degraded by the bis(perfluoroalkylsulfonyl)imide acid, which is a source material. Thus, recovery of the production is low. Furthermore, a special safety measure has to be taken since dimethyl ether generated from the side reaction is flammable.

In the method for producing N-methyl bis(perfluoroalkylsulfonyl)imide disclosed in NPL 2, a special safety measure has to be taken since the diazomethane, which is the methylating agent, is an explosive gas. In the method for producing N-alkyl bis(fluorosulfonyl)imide disclosed in NPL 3, the bis(fluorosulfonyl)imide silver salt, which is used as a source material, is expensive. Thus, it is not cost effective.

Thus far, only a few of fluorine-containing N-alkylsulfonylimide compound has been known. There is no report synthesizing an N-alkyl bis(perfluoroalkylsulfonyl)imide having a perfluoroalkyl group, the number of carbon atoms of which is 2 or 3, an N-alkyl bis(perfluoroalkylsulfonyl)imide having an alkyl group, the number of carbon atoms of which is an integer of 2 or more, and an N-alkyl bis(fluorosulfonyl)imide having an alkyl group, the number of carbon atoms of which is an integer of 3 or more.

Usefulness of ionic liquids as an electrolyte of batteries and capacitors, a solvent for a chemical reaction, a catalyst, or the like, is well recognized. In the conventional method for producing the ionic liquid, the salt replacement shown in a chemical reaction equation shown below is commonly performed. In the equation, salts are exchanged between a fluorine-containing sulfonylimide acid salt and a halogenated salt of a quaternary amine, such as imidazolium bromide salt.

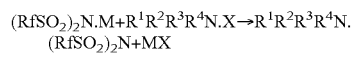
$(RfSO_2)_2N+MX$

However, it is difficult to remove the by-product salt (MX) completely in the conventional ionic liquid production method with the reaction equation shown above, since the ionic liquid, which is the intended product, dissolves the by-product salt. Because of the reason described above, in the conventional method for producing the ionic liquid, it has been difficult to produce a highly pure ionic liquid with a high recovery rate.

The present invention has been made under the circumstances described above. Specifically, a purpose of the present invention is to provide N-alkyl bis(fluorosulfonyl)imide having a perfluoroalkyl group, a number of carbon atoms of which is 2 or 3, or having an alkyl group, a number of carbon atoms of which is an integer of 2 or more. Another purpose of the present invention is to provide N-alkyl bis(fluorosulfonyl) imide having an alkyl group, a number of carbon atoms of which is an integer of 3 or more.

Another purpose of the present invention is to provide a method for producing fluorine-containing N-alkylsulfonylimide compound, which has a high recovery rate and is easy to handle.

In the present invention, the fluorine-containing alkylsulfonylimide compound means N-alkyl bis(perfluoroalkylsulfonyl)imide and N-alkyl bis(fluorosulfonyl)imide.

In addition, another purpose of the present invention is to provide a method for producing a highly pure ionic compound with a high recovery rate.

Solution to Problem

The present invention provides a fluorine-containing N-alkylsulfonylimide compound that is represented by a formula (1) below.

Rf in the formula (1) is a fluorine atom or a perfluoroalkyl group, the number of carbon atoms of which is an integer from 1 to 4.

Also, R in the formula (1) is an alkyl group, the number of carbon atoms of which is an integer of 1 or more. In the fluorine-containing N-alkylsulfonylimide, Rf in the formula (1) may be a perfluoroalkyl group, the number of carbon atoms of which is 2 or 3. In the fluorine-containing N-alkylsulfonylimide, Rf in the formula (1) may be a perfluoroalkyl group, the number of carbon atoms of which is an integer from 1 to 4, and R in the formula (1) may be an alkyl group, the number of carbon atoms of which is an integer of 2 or more. Furthermore, In the fluorine-containing N-alkylsulfonylimide, Rf in the formula (1) is a fluorine atom, and R in the formula (1) may be an alkyl group, the number of carbon atoms of which is an integer of 3 or more.

The present invention also provides a method for producing a fluorine-containing N-alkylsulfonylimide compound comprising the step of: alkylating, in which a fluorine-containing sulfonylimide acid represented by a formula (2) below or a fluorine-containing sulfonylimide acid salt represented by a formula (3) below is alkylated with a dialkylsulfuric acid represented by a formula (4) below or a dialkylcarbonic acid represented by a formula (5) below.

(2)

(3)

(4)

(5)

Rf in the formulae (2) and (3) is a fluorine atom or a perfluoroalkyl group, the number of carbon atoms of which is an integer from 1 to 4. Also, M in the formula (3) is an element selected from the group consisting of Li, Na, and K. Also, R in the formulae (4) and (5) is an alkyl group, a number of carbon atoms of which is an integer of 1 or more. In the method for producing a fluorine-containing N-alkylsulfonylimide compound, the dialkylsulfuric acid represented by the formula (4) or the dialkylcarbonic acid represented by the formula (5) may be added to the fluorine-containing sulfonylimide acid represented by the formula (2) or the fluorine-containing sulfonylimide acid salt represented by the formula (3) in a molar ratio of 50:1 to 1:1 to alkylate the fluorine-containing sulfonylimide acid represented by the formula (2) or the fluorine-containing sulfonylimide acid salt represented by the formula (3). Also, in the method for producing a fluorine-containing N-alkylsulfonylimide compound, a solvent, in which the solubility of the fluorine-containing N-alkylsulfonylimide compound is 100 g/L or lower, may be added to perform the step of alkylation. Furthermore, in the method for producing a fluorine-containing N-alkylsulfonylimide compound, the step of alkylation may be performed under an acidic condition. Furthermore, the method for producing a fluorine-containing N-alkylsulfonylimide compound may further include the step of: decomposing in which water is added after the step of the alkylating and an unreacted part of the dialkylsulfuric acid is decomposed.

Also, the present invention also provides a method for producing an ionic compound including the step of: alkylating a compound producing a cation by alkylation, in which the compound producing a cation by alkylation is alkylated with the fluorine-containing N-alkylsulfonylimide compound described above. In the method for producing an ionic compound, the compound producing cation by alkylation may be a tertiary amine including tri-alkylamine, alkylimidazole, alkylpyridine, alkylpyrrolidine, and alkylpiperidine.

Advantageous Effects of Invention

According to the fluorine-containing N-alkylsulfonylimide compound of the present invention, N-alkyl bis(perfluoroalkylsulfonyl)imide and N-alkyl bis(fluorosulfonyl)imide, which are regarded as promising materials of the ionic liquid free of halogens and alkaline metals, is provided.

According to the method for producing a fluorine-containing N-alkylsulfonylimide compound of the present invention, the fluorine-containing N-alkylsulfonylimide compound represented by the formula (1) above can be produced with a high recovery, since the dialkylsulfuric acid represented by the formula (4) or the dialkylcarbonic acid represented by the formula (5) is used as an alkylating agent. Also, in the method, a special caution is not required in handling, since there is no usage or generation of flammable gas. Therefore, a production method that can be handled easily can be provided.

According to the method for producing an ionic compound, the ionic compound can be synthesized with an imide anion in single step reaction, since the compound producing a cation by alkylation is alkylated using the fluorine-containing N-alkylsulfonylimide compound as an alkylating agent. Also, a highly pure ionic liquid can be obtained with a high recovery rate, since the fluorine-containing N-alkylsulfonylimide compound is the synthetic raw material of the ionic liquid free of halogens and alkaline metals. Particularly, in the case where the ionic compound is synthesized using the N-alkyl bis(perfluoroalkylsulfonyl)imide having a perfluoroalkyl group, a number of carbon atoms of which is 2 or 3 as a raw material, a wide variety of the ionic liquid having the boiling point of 100° C. or lower can be obtained.

BEST MODE FOR CARRYING OUT THE INVENTION

The fluorine-containing N-alkylsulfonylimide compound of the present invention is explained in detail below.

The fluorine-containing N-alkylsulfonylimide compound of the present invention is one of fluorine-containing N-alkylsulfonylimide compounds selected from those represented by a formula (6) below.

(6)

In the formula (6), Rf is a fluorine atom or a perfluoroalkyl group, the number of carbon atoms of which is an integer from 1 to 4.

In addition, R is an alkyl group, the number of carbon atoms of which is an integer of 1 or more N-methyl bis(fluorosulfonyl)imide (($FSO_2$)$_2$NCH$_3$), N-methyl bis(trifluoromethanesulfonyl)imide (($CF_3SO_2$)$_2$NCH$_3$), N-methyl bis(pentafluoroethanesulfonyl)imide (($C_2F_5SO_2$)$_2$NCH$_3$), N-methyl bis(heptafluoropropanesulfonyl)imide (($C_3F_7SO_2$)$_2$NCH$_3$), and N-methyl bis(nonafluorobutanesulfonyl)imide (($C_4F_9SO_2$)$_2$NCH$_3$) are examples of the fluorine-containing N-alkylsulfonylimide compound, in which R is a methyl group, the number of carbon atoms of which is 1.

In the case where the alkyl group (R) is the methyl group, fluorine-containing N-alkylsulfonylimide compounds having the perfluoroalkyl group (Rf), the number of carbon atoms of which is 2 or 3, have not been known. These fluorine-containing N-alkylsulfonylimide compounds having the methyl group and the perfluoroalkyl group (Rf), the number of carbon atoms of which is 2 or 3, are preferable materials for synthesizing the ionic liquid. Particularly, N-methyl bis(pentafluoroethanesulfonyl)imide ($(C_2F_5SO_2)_2NCH_3$) and N-methyl bis(heptafluoropropanesulfonyl)imide ($(C_3F_7SO_2)_2NCH_3$) are even more preferable.

Also, in the fluorine-containing N-alkylsulfonylimide compounds represented by the formula (6) above, ones having Rf being a perfluoroalkyl group, the number of carbon atoms of which is an integer from 1 to 4 and R being an alkyl group, the number of carbon atoms of which is an integer of 2 or more have not been known. These fluorine-containing N-alkylsulfonylimide compounds having Rf being a perfluoroalkyl group, the number of carbon atoms of which is an integer from 1 to 4 and R being an alkyl group, the number of carbon atoms of which is an integer of 2 or more are preferable materials for synthesizing the ionic liquid. N-ethyl bis(trifluoromethanesulfonyl)imide ($(CF_3SO_2)_2NC_2H_5$), N-ethyl bis(pentafluoroethanesulfonyl)imide ($(C_2F_5SO_2)_2NC_2H_5$), N-ethyl bis(heptafluoropropanesulfonyl)imide ($(C_3F_7SO_2)_2NC_2H_5$), and N-ethyl bis(nonafluorobutanesulfonyl)imide ($(C_4F_9SO_2)_2NC_2H_5$) are examples of the fluorine-containing N-alkylsulfonylimide compounds having R being the ethyl group, the number of carbon atoms of which is 2. N-propyl bis(trifluoromethanesulfonyl)imide ($(CF_3SO_2)_2NC_3H_7$), N-propyl bis(pentafluoroethanesulfonyl)imide ($(C_2F_5SO_2)_2NC_3H_7$), N-propyl bis(heptafluoropropanesulfonyl)imide ($(C_3F_7SO_2)_2NC_3H_7$), N-propyl bis(nonafluorobutanesulfonyl)imide ($(C_4F_9SO_2)_2NC_3H_7$) are examples of the fluorine-containing N-alkylsulfonylimide compounds having R being the propyl group, the number of carbon atoms of which is 3.

Also, in the fluorine-containing N-alkylsulfonylimide compounds represented by the formula (6) above, ones having Rf being a fluorine atom and R being an alkyl group, the number of carbon atoms of which is an integer of 3 or more, have not been known. These fluorine-containing N-alkylsulfonylimide compounds having Rf being a fluorine atom and R being an alkyl group, the number of carbon atoms of which is an integer of 3 or more, are preferable materials for synthesizing the ionic liquid. N-propyl bis(fluorosulfonyl)imide ($(FSO_2)_2NC_3H_7$) is an example of the fluorine-containing N-alkylsulfonylimide compound, in which R is a propyl group, the number of carbon atoms of which is 3. N-butyl bis(fluorosulfonyl)imide ($(FSO_2)_2NC_4H_9$) is an example of the fluorine-containing N-alkylsulfonylimide compound, in which R is a butyl group, the number of carbon atoms of which is 4.

In the present invention, it is possible to provide the fluorine-containing N-alkylsulfonylimide compounds that have not been known, by configuring the number of carbon atoms of the perfluoroalkyl group (Rf) to 2 or 3 in the case where the alkyl group (R) is the methyl group, by configuring the number of carbon atoms of the perfluoroalkyl group (Rf) to an integer from 1 to 4 in the case where the number of carbon atoms in the alkyl group (R) is an integer of 2 or more, and by configuring the number of carbon atoms of the perfluoroalkyl group (Rf) to an integer from 1 to 4 in the case where the number of carbon atoms in the alkyl group (R) is an integer of 3 or more. Furthermore, by synthesizing the ionic compounds using the fluorine-containing N-alkylsulfonylimide compounds as raw materials in a single step reaction, the ionic liquid free of halogens and alkaline metals can be obtained.

The N-alkyl bis(perfluoroalkylsulfonyl)imide having the perfluoroalkyl group, a number of carbon atoms are 2 or 3 are particularly useful as a raw material of the ionic liquid free of halogens and alkaline metals, since a wide variety of the ionic liquid having the boiling point of 100° C. or lower can be obtained when these N-alkyl bis(perfluoroalkylsulfonyl)imides are used as the raw material to synthesize the ionic compounds.

Next, the method for producing a fluorine-containing N-alkylsulfonylimide compound of the present invention is explained in detail below.

In the method for producing a fluorine-containing N-alkylsulfonylimide compound of the present invention, fluorine-containing sulfonylimide acid represented by a formula (7) below or fluorine-containing sulfonylimide acid salt represented by a formula (8) below is used as a raw material. The fluorine-containing sulfonylimide acid or the fluorine-containing sulfonylimide acid salt is alkylated by addition of dialkylsulfuric acid represented by a formula (9) below or dialkylcarbonic acid represented by a formula (10) in a molar ratio of 50:1 to 1:1 as an alkylating agent.

$$(RfSO_2)_2NH \tag{7}$$

$$(RfSO_2)_2N.M \tag{8}$$

$$(RO)_2SO_2 \tag{9}$$

$$(RO)_2CO \tag{10}$$

In the case where the fluorine-containing sulfonylimide acid represented by the formula (7) is used as a raw material and the dialkylsulfuric acid represented by the formula (9) is used as an alkylating agent, a chemical reaction represented by a chemical reaction equation (11) shown below is allowed to proceed, producing the fluorine-containing N-alkylsulfonylimide and sulfuric acid ($H_2SO_4$).

$$2(RfSO_2)_2NH+(RO)_2SO_2 \rightarrow 2(RfSO_2)_2NR+H_2SO_4 \tag{11}$$

In the case where the fluorine-containing sulfonylimide acid represented by the formula (7) is used as a raw material and the dialkylcarbonic acid represented by the formula (10) is used as an alkylating agent, a chemical reaction represented by a chemical reaction equation (12) shown below is allowed to proceed, producing the fluorine-containing N-alkylsulfonylimide, carbon dioxide ($CO_2$), and alcohol (ROH).

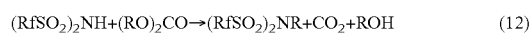
$$(RfSO_2)_2NH+(RO)_2CO \rightarrow (RfSO_2)_2NR+CO_2+ROH \tag{12}$$

In the case where the fluorine-containing sulfonylimide acid salt represented by the formula (8) is used as a raw material and the dialkylsulfuric acid represented by the formula (9) is used as an alkylating agent, a chemical reaction represented by a chemical reaction equation (13) shown below is allowed to proceed, producing the fluorine-containing N-alkylsulfonylimide and sulfuric acid salt ($M_2SO_4$).

$$2(RfSO_2)_2N.M+(RO)_2SO_2 \rightarrow 2(RfSO_2)_2NR+M_2SO_4 \tag{13}$$

In the case where the fluorine-containing sulfonylimide acid salt represented by the formula (8) is used as a raw material and the dialkylcarbonic acid represented by the formula (10) is used as an alkylating agent, a chemical reaction represented by a chemical reaction equation (14) shown below is allowed to proceed under an acidic condition, such as in the presence of sulfuric acid, producing the fluorine-containing N-alkylsulfonylimide, carbon dioxide ($CO_2$), alcohol (ROH), and sulfuric acid salt ($M_2SO_4$).

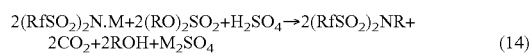
$$2(RfSO_2)_2N.M+2(RO)_2SO_2+H_2SO_4 \rightarrow 2(RfSO_2)_2NR+ 2CO_2+2ROH+M_2SO_4 \tag{14}$$

In the formulae (7) and (8) above, Rf is a fluorine atom or a perfluoroalkyl group, the number of carbon atoms of which is an integer from 1 to 4. Bis(fluorosulfonyl)imide acid (($FSO_2)_2NH$), bis(trifluoromethanesulfonyl)imide acid (($CF_3SO_2)_2NH$), bis(pentafluoroethanesulfonyl)imide acid $((C_2F_5SO_2)_2NH)$, bis(heptafluoropropanesulfonyl)imide acid $((C_3F_7SO_2)_2NH)$, and bis(nonafluorobutanesulfonyl)imide acid $((C_4F_9SO_2)_2NH)$ are examples of the fluorine-containing sulfonylimide acid represented by the formula (7).

Bis(fluorosulfonyl)imide acid salt $((FSO_2)_2N.M)$, bis(trifluoromethanesulfonyl)imide acid salt $((CF_3SO_2)_2N.M)$, bis(pentafluoroethanesulfonyl)imide acid salt $((C_2F_5SO_2)_2N.M)$, bis(heptafluoropropanesulfonyl)imide acid salt $((C_3F_7SO_2)_2N.M)$, and bis(nonafluorobutanesulfonyl)imide acid salt $((C_4F_9SO_2)_2N.M)$ are examples of the fluorine-containing sulfonylimide acid salt represented by the formula (8). In the formula (8), M is an element selected from the group consisting of Li, Na, and K. Thus, more specifically, bis(fluorosulfonyl)imide acid lithium salt $((FSO_2)_2N.Li)$, bis(fluorosulfonyl)imide acid sodium salt $((FSO_2)_2N.Na)$, bis(fluorosulfonyl)imide acid potassium salt $((FSO_2)_2N.K)$, bis(trifluoromethanesulfonyl)imide acid lithium salt $((CF_3SO_2)_2N.Li)$, bis(trifluoromethanesulfonyl)imide acid sodium salt $((CF_3SO_2)_2N.Na)$, bis(trifluoromethanesulfonyl)imide acid potassium salt $((CF_3SO_2)_2N.K)$, bis(pentafluoroethanesulfonyl)imide acid lithium salt $((C_2F_5SO_2)_2N.Li)$, bis(pentafluoroethanesulfonyl)imide acid sodium salt $((C_2F_5SO_2)_2N.Na)$, bis(pentafluoroethanesulfonyl)imide acid potassium salt $((C_2F_5SO_2)_2N.K)$, bis(heptafluoropropanesulfonyl)imide acid lithium salt $((C_3F_7SO_2)_2N.Li)$, bis(heptafluoropropanesulfonyl)imide acid sodium salt $((C_3F_7SO_2)_2N.Na)$, bis(heptafluoropropanesulfonyl)imide acid potassium salt $((C_3F_7SO_2)_2N.K)$, bis(nonafluorobutanesulfonyl)imide acid lithium salt $((C_4F_9SO_2)_2N.Li)$, bis(nonafluorobutanesulfonyl)imide acid sodium salt $((C_4F_9SO_2)_2N.Na)$, and bis(nonafluorobutanesulfonyl)imide acid potassium salt $((C_4F_9SO_2)_2N.K)$ are examples of the fluorine-containing sulfonylimide acid salt represented by the formula (8).

In the formulae (9) and (10) above, R is an alkyl group, the number of carbon atoms of which is an integer of 1 or more. Thus, dimethylsulfuric acid $((CH_3O)_2SO_2)$, diethylsulfuric acid $((C_2H_5O)_2SO_2)$, dipropylsulfuric acid $((C_3H_7O)_2SO_2)$, dibutylsulfuric acid $((C_4H_9O)_2SO_2)$, and the like are examples of the dialkylsulfuric acid represented by the formula (9). Also, dimethylcarbonic acid $((CH_3O)_2CO)$, diethylcarbonic acid $((C_2H_5O)_2CO)$, dipropylcarbonic acid $((C_3H_7O)_2CO)$, dibutylcarbonic acid $((C_4H_9O)_2CO)$, and the like are examples of the dialkylcarbonic acid represented by the formula (10).

In the case where the fluorine-containing sulfonylimide acid salt represented by the formula (8) above is used as a raw material, in which reactions shown by the chemical reaction equations (13) and (14) are allowed to proceed, it is preferable to perform the alkylation under an acidic condition. Because of this, the alkylation reaction of the fluorine-containing sulfonylimide acid salt can be enhanced.

As an example of the present invention, the production method in the case where the fluorine-containing sulfonylimide acid represented by the formula (7) is used as a raw material and the dialkylsulfuric acid represented by the formula (9) is used as an alkylating agent is explained specifically.

First, fluorine-containing sulfonylimide acid, which is a raw material, is placed in a reaction container. Then, excess amount of dialkylsulfuric acid, which is an alkylating agent, relative to the raw material is added to the reaction container. Then, the content of the reaction container is mixed for 1 to 4 hours, while the temperature of the reaction container is kept at about 100° C., allowing alkylation to proceed. Then, the fluorine-containing N-alkylsulfonylimide, which is the product of the reaction, is recovered by a method such as filtration or the like.

It is preferable to add the alkylating agent to the raw material in a molar ratio of 50:1 to 1:1. If the molar ratio of the alkylating agent to the raw material was less than 1:1, the production reaction shown by the reaction equation (11) above would not be allowed to proceed sufficiently. This also makes it difficult to handle the precipitated product. Thus, having the molar ratio less than 1:1 is not preferable. On the other hand, if the molar ratio was more than 50:1, production efficiency would be reduced, and cost for the production would be increased unnecessary. Thus, having the molar ratio more than 50:1 is not preferable.

Contrary to that, if the added amount of the alkylating agent was in the range described above, the production reaction shown by the reaction equation (11) above would be allowed to proceed efficiently. Also, the dialkylsulfuric acid, which is the alkylating agent, is a poor solvent of the fluorine-containing N-alkylsulfonylimide, which is the product of the reaction. The solubility of the fluorine-containing N-alkylsulfonylimide in the dialkylsulfuric acid is less than 100 g/L. Thus, in the reaction system where alkylating agent is added to the raw material in a molar ratio of 5:1 to 30:1, the reaction product is not dissolved in the alkylating agent and precipitated. Because of this, the production reaction shown in the reaction equation (11) can be enhanced further. As a result, the fluorine-containing N-alkylsulfonylimide can be produced with a high efficiency.

In this example, a preferable reaction temperature ranges from 0 to 200° C. An even more preferable reaction temperature ranges from 50 to 150° C.

In this examples, a preferable reaction time ranges from 0.5 to 200 hours. An even more preferable reaction temperature ranges from 1 to 50 hours.

In the case where the reaction product is the fluorine-containing N-alkylsulfonylimide represented by the formula (6), in which Rf is a perfluoroalkyl group, the number of carbon atoms of which is an integer from 2 to 4 and R is a methyl group, the number of carbon atoms of which is 1, the reaction product is precipitated from the system in solid state. Thus, the product can be recovered easily from the reaction system by filtration.

As an alternative example of the method for producing the fluorine-containing N-alkylsulfonylimide compound of the present invention, a poor solvent to the fluorine-containing N-alkylsulfonylimide, which is a reaction product, can be added to the reaction system. In this example, a preferable poor solvent is one to which the solubility of the fluorine-containing N-alkylsulfonylimide is 100 g/L or less. An even more preferable solvent is one to which the solubility of the fluorine-containing N-alkylsulfonylimide is 10 g/L or less. Specifically, aprotic polar solvents, chlorinated solvent, or the like are examples of the poor solvent to the reaction product. More specifically, acetonitrile $(CH_3CN)$, dimethylsulfoxide $(CH_3SO)$, or the like are examples of the aprotic polar solvents. Chloroform $(CHCl_3)$ or the like is an example of the chlorinated solvent.

In this example, by adding the poor solvent to which the solubility of the fluorine-containing N-alkylsulfonylimide is 100 g/L or less into the reaction system, the reaction product is precipitated in the reaction system instead of being dissolved. Thus, it is easy to separate the reaction product from the reaction system. Furthermore, the producing reaction represented by the formula (11) can be accelerated.

As another alternative example of the method for producing the fluorine-containing N-alkylsulfonylimide compound of the present invention, water can be added to the reaction system after the producing reaction represented by the formulae (11) to (14) to decompose the unreacted alkylating agent. The reaction product can be recovered afterward. By adding water to the reaction system after the producing reaction, the dialkylsulfuric acid, which is the unreacted alkylating agent, is decomposed, producing alcohol and sulfuric acid, as shown in the formula (15) below.

$$(RO)_2SO_2 + 2H_2O \rightarrow 2R\text{—}OH + H_2SO_4 \quad (15)$$

In the case where Rf in the formula (6) above is a fluorine atom or a perfluoroalkyl group, the number of carbon atoms of which is 1 or 2, the produced fluorine-containing N-alkylsulfonylimide is dissolved in the dialkylsulfuric acid remained in the reaction system. As a result, it makes it difficult to separate the product from the reaction system, and its recovery is reduced.

Even though it is difficult to separate the reaction product from the reaction system as in the case described above, by adding water after the reaction and decomposing the unreacted dialkylsulfuric acid or dialkylcarbonic acid, the product dissolved in the dialkylsulfuric acid or dialkylcarbonic acid residing in the reaction system can be separated effectively. In addition, the water added to the reaction system functions as a poor solvent to the produced N-alkyl bis(perfluoroalkylsulfonyl)imide. As a result, the product can be precipitated out effectively from the reaction system by adding water.

As explained above, in the method for producing the fluorine-containing N-alkylsulfonylimide of the present invention, the dialkylsulfuric acid or the dialkylcarbonic acid, which is produced inexpensively in an industrial scale, is used as an alkylating agent. In the method of the present invention, by just adding these inexpensive alkylating agents in excess amount relative to the source material, the fluorine-containing N-alkylsulfonylimide can be produced with a high recovery rate. In addition, the reaction product can be separated easily in this method, since the dialkylsulfuric acid (or dialkylcarbonic acid), acetonitrile, water, or the like is added to the reaction system. In addition, in this production method of the present invention, no flammable gas or the like is formed, even though sulfuric acid, carbon dioxide, sulfuric acid salt, and alcohol are formed beside the intended reaction product as shown in the formulae (11) to (15). Therefore, there is no need to take a special caution to the source materials and reaction products. As a result, a production method that is easy to handle can be provided.

Next, the method for producing an ionic liquid using the fluorine-containing N-alkylsulfonylimide compound of the present invention is explained in detail below.

In the method for producing an ionic liquid of the present invention, a compound producing a cation by alkylation is alkylated by the fluorine-containing N-alkylsulfonylimide compounds.

A preferable compounds producing a cation by alkylation is a tertiary amine or the like, such as tri-alkylamine, alkylimidazole, alkylpyridine, alkylpyrrolidine, and alkylpiperidine. Tri-methylamine, tri-ethylamine, tri-propylamine, dimethylamine, or the like are examples of the tri-alkylamine. methylimidazole, ethylimidazole, propylimidazole, or the like are examples of the alkylimidazole. 3-methylpyridine, 3-ethylpyridine, or the like are examples of alkylpyridine. N-methylpyrrolidine, N-ethylpyrrolidine, or the like are examples of the alkylpyrrolidine. N-methylpiperidine, N-ethylpiperidine, or the like are examples of the alkylpiperidine.

In the case where a tertiary amine is used as the compound producing a cation by alkylation, a chemical reaction represented by the formula (16) is allowed to proceed, producing an ionic compound having the imide anion in the single step reaction.

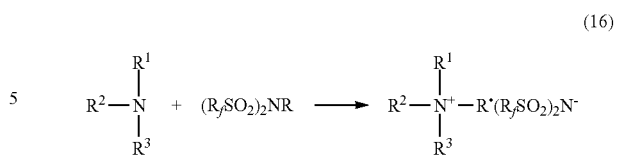

In the case where an alkylimidazole is used as the compound producing a cation by alkylation, a chemical reaction represented by the formula (17) is allowed to proceed, producing an ionic compound having the imide anion in the single step reaction.

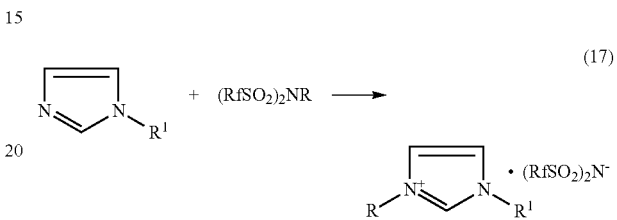

A preferable fluorine-containing N-alkylsulfonylimide compound as the alkylating agent is N-alkyl bis(perfluoroalkylsulfonyl)imide having a perfluoroalkyl group, the number of carbon atoms of which is 2 or 3. By using the N-alkyl bis(perfluoroalkylsulfonyl)imide having a perfluoroalkyl group, the number of carbon atoms of which is 2 or 3 as an alkylating agent, a wide variety of the ionic liquid having the boiling point of 100° C. or lower can be obtained.

As explained above, in the method for producing an ionic liquid of the present invention, a compound producing a cation by alkylation is alkylated by the fluorine-containing N-alkylsulfonylimide compound as an alkylating agent. Because of this configuration, it is possible to synthesize the ionic compound having the imide anion in a single step reaction. In addition, since the N-alkyl bis(perfluoroalkylsulfonyl)imide is a source material of the ionic liquid free of halogens and alkaline metals, it is possible to produce a highly pure ionic liquid with high recovery rate in the method. Particularly, in the case where the ionic compound is synthesized using the N-alkyl bis(perfluoroalkylsulfonyl)imide, the number of carbon atoms of which is 2 or 3 as a source material, a wide variety of the ionic liquid having the boiling point of 100° C. or lower can be obtained.

EXAMPLES

The advantageous effect of the present invention is explained in detail with Examples below. The present invention is not limited to a configuration detailed in examples.

Example 1

First, 20 g of bis(nonafluorobutanesulfonyl)imide acid (($C_4F_9SO_2)_2NH$) was placed in a 100 ml volume flask as a source material. Then, 65 g of dimethylsulfuric acid (($CH_3O)_2SO_2$) as an alkylating agent was added to the flask. The alkylating agent was added to the source material in a molar ratio of 14:1. After stirring the content of the flask for 4 hours while the temperature inside of the flask was kept at 100° C., the content of the flask was stirred for 1 hour at room temperature. Then, after filtering the reaction liquid, crystals on the filter were washed by 30 g of acetonitrile, and the washed crystals were dried at 40° C. under reduced pressure.

By following this procedure, 17 g of N-methyl bis(nonafluorobutanesulfonyl)imide ($(C_4F_9SO_2)_2NCH_3$) was obtained as a product (yield: 83%).

Example 2

By following the procedure described in Example 1, except for adding the alkylating agent in the molar ratio of 1:1 instead, 15 g of N-methyl bis(nonafluorobutanesulfonyl)imide ($(C_4F_9SO_2)_2NCH_3$) was obtained (yield: 75%).

Example 3

By following the procedure described in Example 2, except for adding 10 g of acetonitrile to the source material and the alkylating agent, 18 g of N-methyl bis(nonafluorobutanesulfonyl)imide ($(C_4F_9SO_2)_2NCH_3$) was obtained as a product (yield: 88%).

Example 4

First, 100 g of bis(nonafluorobutanesulfonyl)imide acid ($(C_4F_9SO_2)_2NH$) was placed in a 500 ml volume flask as a source material. Then, 265 g of dimethylsulfuric acid ($(CH_3O)_2SO_2$) as an alkylating agent was added to the flask. The alkylating agent was added to the source material in a molar ratio of 10:1. Then, the content of the flask was stirred for 20 hours while the temperature inside of the flask was kept at 100° C. In a 1 L volume flask, 550 g of water was placed. To the 1 L volume flask holding the water, the reaction liquid in the first flask was introduced. Then, the content of the 1 L volume flask was stirred for 20 hours while the temperature inside of the flask was kept at 40° C. By decomposing the excess of the diethylsulfuric acid and separating, 99 g of N-ethyl bis(nonafluorobutanesulfonyl)imide ($(C_4F_9SO_2)_2NC_2H_5$) was obtained (yield: 94%).

Example 5

First, 5 g of bis(heptafluoropropanesulfonyl)imide acid ($(C_3F_7SO_2)_2NH$) was placed in a 50 ml volume flask as a source material. Then, 20 g of dimethylsulfuric acid ($(CH_3O)_2SO_2$) as an alkylating agent was added to the flask. The alkylating agent was added to the source material in a molar ratio of 15:1. After stirring the content of the flask for 20 hours while the temperature inside of the flask was kept at 100° C., the content of the flask was stirred for 1 hour at room temperature. Then, the reaction liquid was treated as in Example 4, and 4.7 g of N-methyl bis(heptafluoropropanesulfonyl)imide ($(C_3F_7SO_2)_2NCH_3$) was obtained (yield: 92%).

Example 6

First, 5 g of bis(pentafluoroethanesulfonyl)imide acid ($(C_2F_5SO_2)_2NH$) was placed in a 50 ml volume flask as a source material. Then, 20 g of dimethylsulfuric acid ($(CH_3O)_2SO_2$) as an alkylating agent was added to the flask. The alkylating agent was added to the source material in a molar ratio of 15:1. Then, the content of the flask was stirred for 20 hours while the temperature inside of the flask was kept at 100° C. Then, by distilling the content of the flask under reduced pressure, 5 g of distillate was obtained. By treating this distillate as in Example 4, 4.9 g of N-methyl bis(pentafluoroethanesulfonyl)imide ($(C_2F_5SO_2)_2NCH_3$) was obtained (yield: 95%).

Example 7

First, 3.0 g of bis(nonafluorobutanesulfonyl)imide acid ($(C_4F_9SO_2)_2NH$) was placed in a 100 ml volume flask as a source material. Then, 14.0 g of dimethylcarbonic acid ($(CH_3O)_2CO$) as an alkylating agent was added to the flask. The alkylating agent was added to the source material in a molar ratio of 30:1. Then, the content of the flask was stirred for 6 hours while the temperature inside of the flask was kept at 90° C. Then, by concentrating the reaction liquid, 2.5 g of N-methyl bis(nonafluorobutanesulfonyl)imide ($(C_4F_9SO_2)_2NCH_3$) was obtained (yield: 83%).

Example 8

First, 10.0 g of bis(pentafluoroethanesulfonyl)imide acid potassium salt ($(C_2F_5SO_2)_2NK$) was placed in a 300 ml volume flask as a source material. Then, 45.1 g of dimethylsulfuric acid ($(CH_3O)_2SO_2$) as an alkylating agent was added to the flask. The alkylating agent was added to the source material in a molar ratio of 15:1. After introduction of 2.3 g of concentrated sulfuric acid to the flask, the content of the flask was stirred for 20 hours while the temperature inside of the flask was kept at 100° C. Then, 200 g of water was introduced to the flask, and the content of the flask was stirred for 2 hours at 50° C. Then, by cooling down the flask to room temperature and filtrating the reaction liquid, 8.5 g of N-methyl bis(pentafluoroethanesulfonyl)imide ($(C_2F_5SO_2)_2NCH_3$) was obtained (yield: 90%).

Example 9

First, 10.0 g of bis(pentafluoroethanesulfonyl)imide acid potassium salt ($(C_2F_5SO_2)_2NK$) was placed in a 300 ml volume flask as a source material. Then, 45.1 g of dimethylsulfuric acid ($(CH_3O)_2SO_2$) as an alkylating agent was added to the flask. The alkylating agent was added to the source material in a molar ratio of 15:1. After stirring the content of the flask for 1 hour while the temperature inside of the flask was kept at 100° C., the entire reaction liquid was gelated. Thus, the gelated liquid was kept at 100° C. for 19 hours later on. Then, 200 g of water was introduced to the flask, and the content of the flask was stirred for 2 hours at 50° C. By cooling down the reaction liquid to room temperature and filtering, 5.2 g of N-methyl bis(pentafluoroethanesulfonyl)imide ($(C_2F_5SO_2)_2NCH_3$) was obtained (yield: 55%).

Example 10

Synthesis of N-methyl bis(fluorosulfonyl)imide

In a 100 ml volume flask equipped with a stirring bar, a condenser tube, and a thermometer, 86.4 g (685.5 mmol) of dimethylsulfuric acid X($(CH_3O)_2SO_2$), 10.0 g (45.7 mmol) of bis(fluorosulfonyl)imide acid potassium salt ($(FSO_2)_2NK$), and 4.0 g (45.7 mmol) of dioxane ($O(CH_2CH_2)_2O$) were placed. Then, the content of the flask was stirred for 2 hours at 100° C. After pouring 150 g of ion-exchange water, the content of the flask was stirred for 1 hour at 70° C. After the stirring, by separating with a separating funnel, 4.0 g of N-methyl bis(fluorosulfonyl)imide (lower layer), which was the intended product, was obtained (yield: 45%). Furthermore, after extracting the aqueous phase (upper phase) with chloroform, by concentrating the solvent, 2.6 g of the intended product was obtained (total yield: 74%).

Example 11

First, 5.0 g of bis(nonafluorobutanesulfonyl)imide acid potassium salt ($(C_4F_9SO_2)_2NK$) was placed in a 100 ml volume flask as a source material. Then, 21.8 g of dimethylcarbonic acid (($CH_3O$)$_2$CO) as an alkylating agent was added to the flask. The alkylating agent was added to the source material in a molar ratio of 30:1. After adding 2.4 g of concentrated sulfuric acid into the flask, the content of the flask was stirred for 24 hours while the temperature inside of the flask was kept at 95° C. Then, 50.0 g of water was introduced to the flask, and the content of the flask was stirred for 2 hours at 50° C. By cooling down the reaction liquid to room temperature, filtering it, and drying it under reduced pressure, 4.0 g of N-methyl bis(nonafluorobutanesulfonyl)imide (($C_4F_9SO_2$)$_2NCH_3$) was obtained (yield: 83%).

Example 12

Synthesis of 1-ethyl-3-methylimidazolium bis(pentafluoroethanesulfonyl)imide

In a 50 ml volume flask equipped with a stirring bar, a condenser tube, and a thermometer, 35.0 g (85.6 mmol) of N-ethyl bis(pentafluoroethanesulfonyl)imide (($C_2F_5SO_2$)$_2NC_2H_5$) was placed. The flask was heated to 80° C. Into the heated flask, 7.4 g (90.2 mmol) of methylimidazole was dripped, and the flask was stirred for 1 hour at 75° C. After the stirring, by vacuum drying the reaction liquid for 3 hours in the pressure of 2 to 3 Ton at 100° C., 41.6 g of 1-ethyl-3-methylimidazolium bis(pentafluoroethanesulfonyl)imide was obtained (yield: 99%). The melting point of the preparation was −3 to −4° C.

Example 13

Synthesis of 1-ethyl-3-methylimidazolium bis(heptafluoropropanesulfonyl)imide

In a 50 ml volume flask equipped with a stirring bar, a condenser tube, and a thermometer, 40.0 g (78.6 mmol) of N-ethyl bis(heptafluoropropanesulfonyl)imide (($C_3F_7SO_2$)$_2NC_2H_5$) was placed. The flask was heated to 90° C. Into the heated flask, 6.8 g (82.9 mmol) of methylimidazole was dripped, and the flask was stirred for 1 hour at 95° C. After the stirring, by vacuum drying the reaction liquid for 3 hours in the pressure of 2 to 3 Torr at 100° C., 45.5 g of 1-ethyl-3-methylimidazolium bis(heptafluoropropanesulfonyl)imide was obtained (yield: 98%). The melting point of the preparation was 32 to 33° C.

Comparative Example 1

First, 20 g of bis(nonafluorobutanesulfonyl)imide acid (($C_4F_9SO_2$)$_2$NH) was placed in a 100 ml volume flask as a source material. Then, 58 g of trimethyl orthoacetate ($CH_3C(OCH_3)_3$) as an alkylating agent was added to the flask. The alkylating agent was added to the source material in a molar ratio of 14:1. After adding the trimethyl orthoacetate, dimethyl ether was formed immediately.

Then, the reaction liquid was refluxed for 3 hours while the temperature inside of the flask was kept at 60° C. Then, the composition of the reaction liquid was analyzed with $^1$H-NMR and $^{19}$F-NMR. In the analysis, in addition to the intended reaction product, bis(nonafluorobutanesulfonyl) imide, which is the source material, and methyl acetate were detected. The trimethyl orthoacetate, which was fed excessively, was disappeared and degraded into methyl acetate and dimethyl ether.

Next, 29 g of trimethyl orthoacetate was further added, and the reaction liquid was refluxed for 20 hours. Then, methyl acetate in the reaction liquid was distilled away under reduced pressure. Into this concentrated preparation, 50 g of acetonitrile was added, turning the preparation into a slurry. By filtering the slurry, 8 g of N-methyl bis(nonafluorobutanesulfonyl)imide (($C_4F_9SO_2$)$_2NCH_3$), which was the intended reaction product, was obtained (yield: 40%).

Comparative Example 2

First, 20 g of bis(nonafluorobutanesulfonyl)imide acid (($C_4F_9SO_2$)$_2$NH) was placed in a 100 ml volume flask as a source material. Then, 2 g of dimethylsulfuric acid (($CH_3O$)$_2SO_2$) as an alkylating agent was added to the flask. The alkylating agent was added to the source material in a molar ratio of 0.5:1. Then, the content of the flask was stirred while the temperature inside of the flask was kept at 100° C., and the reaction rate of N-methyl bis(nonafluorobutanesulfonyl)imide (($C_4F_9SO_2$)$_2NCH_3$), which was the reaction product, was monitored by $^{19}$F-NMR. The monitoring showed that once the reaction rate reached to 25% after 40 hours, there was no further increase of the reaction rate.

INDUSTRIAL APPLICABILITY

The present invention relates to a fluorine-containing N-alkylsulfonylimide compound, a method of producing a fluorine-containing N-alkylsulfonylimide compound, and a method of producing an ionic compound. According to the method for producing a fluorine-containing N-alkylsulfonylimide compound of the present invention, a fluorine-containing N-alkylsulfonylimide compound can be produced with a high recovery rate, since dialkylsulfuric acid or dialkylcarbonic acid is used as an alkylating agent.

The invention claimed is:

1. A fluorine-containing N-alkylsulfonylimide compound represented by the formula (1),

$(RfSO_2)_2NR$         (1), wherein, Rf in the formula (1) is a perfluoroalkyl group, a number of carbon atoms of which is an integer from 1 to 4, and R in the formula (1) is an alkyl group, a number of carbon atoms of which is an integer of 2 or more.

2. A method for producing a fluorine-containing N-alkylsulfonylimide compound comprising the step of:

alkylating, in which a fluorine-containing sulfonylimide acid represented by a formula (2) below or a fluorine-containing sulfonylimide acid salt represented by a formula (3) below is alkylated with a dialkylsulfuric acid represented by a formula (4) below or a dialkylcarbonic acid represented by a formula (5) below,

$(RfSO_2)_2NH$         (2),

$(RfSO_2)_2N.M$         (3),

$(RO)_2SO_2$         (4),

$(RO)_2CO$         (5), wherein, Rf in the formulae (2) and (3) is a fluorine atom or a perfluoroalkyl group, a number of carbon atoms of which is an integer from 1 to 4, M in the formula (3) is an element selected from the group consisting of Li, Na, and K, and R in the formulae (4) and (5) is an alkyl group, a number of carbon atoms of which is an integer of 1 or more.

3. A method for producing a fluorine-containing N-alkylsulfonylimide compound according to claim 2, wherein, the dialkylsulfuric acid represented by the formula (4) or the dialkylcarbonic acid represented by the formula (5) is added to the fluorine-containing sulfonylimide acid represented by the formula (2) or the fluorine-containing sulfonylimide acid salt represented by the formula (3) in a molar ratio of 50:1 to 1:1 to alkylate the fluorine-containing sulfonylimide acid represented by the formula (2) or the fluorine-containing sulfonylimide acid salt represented by the formula (3).

4. A method for producing a fluorine-containing N-alkylsulfonylimide compound according to claim 2,
wherein a solvent, in which the solubility of the fluorine-containing N-alkylsulfonylimide compound is 100 g/L or lower, is added to perform the step of alkylation.

5. A method for producing a fluorine-containing N-alkylsulfonylimide compound according to claim 2,
wherein the step of alkylation is performed under an acidic condition.

6. A method for producing a fluorine-containing N-alkylsulfonylimide compound according to claim 4,
wherein the step of alkylation is performed under an acidic condition.

7. A method for producing a quaternary ammonium salt comprising the step of:
alkylating a tertiary amine, in which the tertiary amine is alkylated with the fluorine-containing N-alkylsulfonylimide compound represented by formula (1),

$$(RfSO_2)_2NR \qquad (1),$$

wherein, Rf in the formula (1) is a fluorine atom or a perfluoroalkyl group, a number of carbon atoms of which is an integer from 1 to 4, and
R in the formula (1) is an alkyl group, a number of carbon atoms of which is an integer of 1 or more.

8. A method for producing a quaternary ammonium salt according to claim 7,
wherein, the tertiary amine is a tri-alkylamine, an alkylimidazole, an alkylpyridine, an alkylpyrrolidine, or an alkylpiperidine.

9. A method for producing a fluorine-containing N-alkylsulfonylimide compound according to claim 2 further comprising the step of:
decomposing in which water is added after the step of the alkylating and an unreacted part of the dialkylsulfuric acid is decomposed.

10. A method for producing a fluorine-containing N-alkylsulfonylimide compound according to claim 4 further comprising the step of:
decomposing in which water is added after the step of the alkylating and an unreacted part of the dialkylsulfuric acid is decomposed.

11. A method for producing a fluorine-containing N-alkylsulfonylimide compound according to claim 5 further comprising the step of:
decomposing in which water is added after the step of the alkylating and an unreacted part of the dialkylsulfuric acid is decomposed.

12. A method for producing a fluorine-containing N-alkylsulfonylimide compound according to claim 6 further comprising the step of:
decomposing in which water is added after the step of the alkylating and an unreacted part of the dialkylsulfuric acid is decomposed.

13. A method for producing a fluorine-containing N-alkylsulfonylimide compound according to claim 3,
wherein a solvent, in which the solubility of the fluorine-containing N-alkylsulfonylimide compound is 100 g/L or lower, is added to perform the step of alkylation.

14. A method for producing a fluorine-containing N-alkylsulfonylimide compound according to claim 3,
wherein the step of alkylation is performed under an acidic condition.

15. A method for producing a quaternary ammonium salt according to claim 7,
wherein Rf in formula (1) is a perfluoroalkyl group, a number of carbon atoms of which is 2 or 3.

16. A method for producing a quaternary ammonium salt according to claim 7,
wherein, Rf in formula (1) is a perfluoroalkyl group, a number of carbon atoms of which is an integer from 1 to 4, and
R in formula (1) is an alkyl group, a number of carbon atoms of which is an integer of 2 or more.

17. A method for producing a quaternary ammonium salt according to claim 7,
wherein, Rf in the formula (1) is a fluorine atom, and
R in the formula (1) is an alkyl group, a number of carbon atoms of which is an integer of 3 or more.

18. A method for producing a fluorine-containing N-alkylsulfonylimide compound according to claim 3 further comprising the step of:
decomposing in which water is added after the step of the alkylating and an unreacted part of the dialkylsulfuric acid is decomposed.

* * * * *